United States Patent [19]

Rizk et al.

[11] Patent Number: 5,297,440
[45] Date of Patent: Mar. 29, 1994

[54] METHOD AND APPARATUS FOR TESTING THE BENDING CHARACTERISTICS OF SURGICAL NEEDLES

[75] Inventors: Said A. Rizk, Monroe; Alfred G. Evans, Torrington, both of Conn.

[73] Assignee: United States Surgical Corporation, Norwalk, Conn.

[21] Appl. No.: 959,274

[22] Filed: Oct. 9, 1992

[51] Int. Cl.⁵ .............................................. G01N 3/20
[52] U.S. Cl. .................................................... 73/849
[58] Field of Search .................... 73/849, 850, 851, 161

[56] References Cited

U.S. PATENT DOCUMENTS

| | | |
|---|---|---|
| 2,740,296 | 4/1956 | Andres . |
| 3,418,855 | 12/1968 | Apat . |
| 3,817,090 | 6/1974 | Michel ..................... 73/81 |
| 3,902,358 | 9/1975 | Moore ..................... 73/104 |
| 3,955,407 | 5/1976 | Rozett . |
| 3,956,924 | 5/1976 | Hansen et al. ............. 73/81 |
| 4,094,188 | 6/1978 | Bellouin et al. ........... 73/81 |
| 4,160,325 | 7/1979 | DeNicola . |
| 4,194,402 | 3/1980 | De Nicola ............... 73/859 |
| 4,302,967 | 12/1981 | Dufey .................... 73/84 |
| 4,721,000 | 1/1988 | Scanlon ................... 73/833 |
| 4,951,512 | 8/1990 | Mazza et al. ............ 73/861.23 |
| 5,000,912 | 3/1991 | Bendel et al. ........... 420/34 |
| 5,022,273 | 6/1991 | Evans ..................... 73/849 |

FOREIGN PATENT DOCUMENTS

| | | |
|---|---|---|
| 0294210 | 12/1988 | European Pat. Off. . |
| 50136 | of 0000 | Fed. Rep. of Germany . |
| 738878 | 12/1932 | France . |
| 715934 | 2/1980 | U.S.S.R. . |
| 1456111 | 2/1989 | U.S.S.R. . |
| 1298510 | 3/9187 | U.S.S.R. . |
| 1499208 | 1/1978 | United Kingdom . |

OTHER PUBLICATIONS

"Biomechanics of Curved Surgical Needle Bending", *Journal of Biomedical Research*, vol. 23, No. A1, pp. 129-143, 1989.

"A New Quantitative Measurement for Surgical Needle Ductility", *Annals. of Emergency Medicine*, vol. 18, pp. 64-68, Jan. 1989.

"New Developments in Hypodermic Needles" *Bulletin of the Parenteral Drug Association*, vol. 25, No. 6, pp. 270-278, Nov.-Dec. 1971.

"Purchasing Digest/Needle Sharpness Testers", 2 pages, published by Nov. 1988.

Instron Operations Manual No. M10-CR5368-1, Instron Corporation.

*Primary Examiner*—Jerry W. Myracle

[57] ABSTRACT

An apparatus for determining the bending characteristics of a curved surgical needle having a butt end portion and a tip portion including a base support, a clamp for releasably gripping the butt end portion of the needle. A system of stepper motors and related plates is provided for moving the gripped needle along a predetermined path. A load cell is positioned within the predetermined path for engagement by the tip of the needle and for sensing the forces generated by the moving needle tip, and a minimal friction support plate is provided for the load cell to maintain the needle tip at a predetermined location on the load cell while moving the gripped needle.

21 Claims, 6 Drawing Sheets

METHOD AND APPARATUS FOR TESTING THE BENDING CHARACTERISTICS OF SURGICAL NEEDLES

BACKGROUND OF THE INVENTION

1. Field of the Invention

The present invention relates to an apparatus for determining the bending characteristics of an elongated member and more particularly to a method and apparatus for testing the bending characteristics of a curved surgical needle subjected to linear or rotational forces or any combination thereof. In particular, such bending moment deformation facilitates obtaining the bending characteristics of the needle, including bending yield moment, ultimate bending moment, and bending stiffness.

2. Description of the Related Art

While using a curved surgical needle a surgeon must know approximately how much the needle can bend or deform and still retain its original shape. It is well known that at some point the deformation may become permanent. As a force is exerted on an area of a needle, the needle begins to bend and undergo deformation. As with many metals, initially the deformation is elastic, that is, the needle will return to its original shape when the force is removed and no hysteresis will be evident. In the needle art this elastic range is often regarded as a measure of stiffness of the needle.

A needle may be tested for this elastic range by loading and unloading the needle at a particular point and recording the differences in the load data. During elastic deformation the results will be plotted as a straight line on a graph of load vs. angular deformation. At some point the deformation may become permanent, i.e., inelastic. The level of loading which causes permanent deformation is called the yield load, which has been empirically determined to occur at a point where the straight line plot of load vs. strain crosses a line 2° parallel to, and offset from the straight portion of the curve.

There are various devices available to test the bending strengths and yield loads of surgical needles. One known device, the Tinius-Olson Stiffness Tester, is designed to test the bending strength of straight needles by forcing a tip of the needle against a weighted plate and observing the deflection of the plate. Other known devices used to measure the bending strength of curved needles typically employ a projection, such as a peg or knife edge, to intercept a rotating needle somewhere along its length.

One known device is described in commonly assigned U.S. Pat. No. 5,022,273 to Evans, the disclosure of which is incorporated herein by reference. The Evans Patent relates to a needle tester which includes a clamp mounted on a rotary table driven by a stepper motor. Horizontal and vertical manual vernier positioning means are provided to aid in setting an initial position. A knife edge is mounted on a load cell to intercept a rotating needle while undergoing test loads while the load vs. angular deformation of the needle is being recorded. The Evans device is structured to maintain the contact edge equidistant from the center of rotation of the needle during the rotation. This method assumes that the load forces are purely vertical. However, any knife edge, no matter how sharp, has a finite radius of curvature causing a horizontal force component to be introduced and therefore the reaction of a knife edge is a radial force component rather than a true vertical component.

While the recent devices measure the bending strength of a curved surgical needle loaded along its length they provide little information about the behavior of such curved surgical needle when loaded at or near the tip of the needle. For example, the greatest amount of the deformation of the needles will normally occur when loaded at or near the tip. Since the loads on the tip of a needle are generally substantial during penetration of tissue, the bend strength of a needle so loaded is of great interest to surgeons. Furthermore, during such use curved surgical needles are subjected to linear as well as rotational forces and it would therefore be advantageous to test a needle under these compound force conditions.

SUMMARY OF THE INVENTION

An apparatus for determining the bending characteristics of a curved surgical needle having a butt end portion and a tip portion which comprises support means, means associated with the support means for releasably gripping the butt end portion of the needle, means for moving the gripping means and the needle along a predetermined path, means positioned within the predetermined path for engagement by the tip of the needle, means for sensing the forces applied to said engagement means by the needle tip, and means to maintain the needle tip at a predetermined location on the engagement means while moving the gripping means and the needle. Preferably the means for releasably gripping needle comprises clamping means. Further, the means for moving the gripping means preferably comprises a first table arranged and adapted for linear movement. Also, the predetermined path may be defined by linear movement along one or more of three orthogonal axes, the latter being a compound path. Further, the path may be rotational, along or in combination with a linear path or a compound path.

The means for moving the gripped needle may also comprise a second table arranged and adapted for rotational movement and mounted with respect to the linearly movable table for rotatably supporting the needle gripping means. Stepper motors are preferably provided to move the first and second tables. The first table is preferably mounted on bearing support means adapted to facilitate table movement with minimal frictional resistance, and the stepper motors are respectively controlled by controller means adapted to control the motor according to predetermined instructions. Further, the center of rotation of the needle coincides with the center of rotation the second table. The sensing means is preferably in the form of load cell means positioned, adapted and arranged to engage the needle tip.

The needle locating maintaining means preferably includes means to synchronize movement of the first and second tables, and the upper surface of the load cell means is adapted and positioned to engage the needle. Further, minimal friction support means is provided to support the needle locating maintaining means.

According to one embodiment an apparatus is provided for determining the bending characteristics of a curved surgical needle having a butt end and a tip comprising means for releasably gripping the butt end of the needle, means for moving the gripped needle along a path having a plurality of axes, and means positioned within the path of the gripped needle for interaction with the tip of the needle. Means is provided for sensing the forces applied to said interaction means by said needle tip, and means is provided for synchronizing the needle movement to permit deformation of the needle without relative movement between the needle tip and the sensing means. Preferably the means for moving the gripped needle comprises a plurality of movable plates for movable support of the gripping means and the plates are adapted to move in synchronized fashion.

According to the preferred embodiment a load cell is mounted on a low friction plate and a plurality of stepper motors is provided and adapted and arranged for driving the tables to move the elongated needle mounted in the clamp into engagement with the load cell and to provide synchronous movement of the horizontal slide table and the vertical slide table. The frictional resistance to movement of the low friction plate is less than the resistance to movement of the needle tip relative to the load cell to thereby permit uninhibited deformation of the needle.

A method is disclosed for determining the bending characteristics of a curved surgical needle having a butt end portion and a pointed tip comprising releasably gripping the butt end portion of the needle, moving the needle along a predetermined path, obstructing the movement of the tip of the needle, maintaining the position of the tip of the needle on the obstruction, and generating a signal proportional to the forces which the needle tip exerts on said obstruction during said obstructing step.

According to the method the needle is moved along a plurality of axes in synchronized manner to permit the needle to deform while avoiding relative movement between the needle tip and the obstructing means. Further, the obstructing means is load cell means and the signal generating means is a sensor adapted to generate a signal dependent on the forces applied to the load cell means.

BRIEF DESCRIPTION OF THE DRAWINGS

Preferred embodiments of the invention are described hereinbelow with reference to the drawings wherein.

DETAILED DESCRIPTION OF THE PREFERRED EMBODIMENTS

Figure 1:
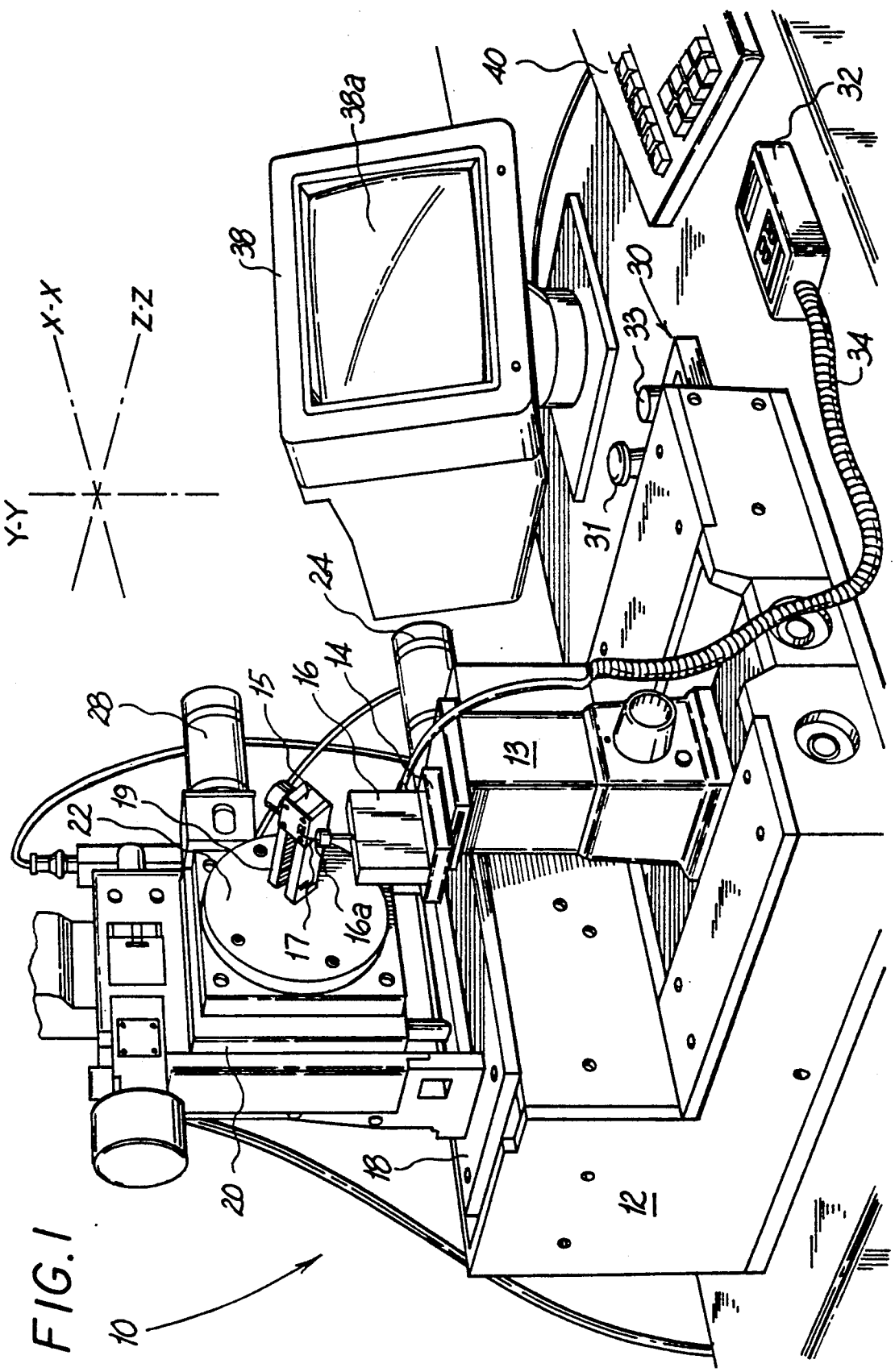
FIG. 1 is an overall perspective view of the present invention.
Figure 2:
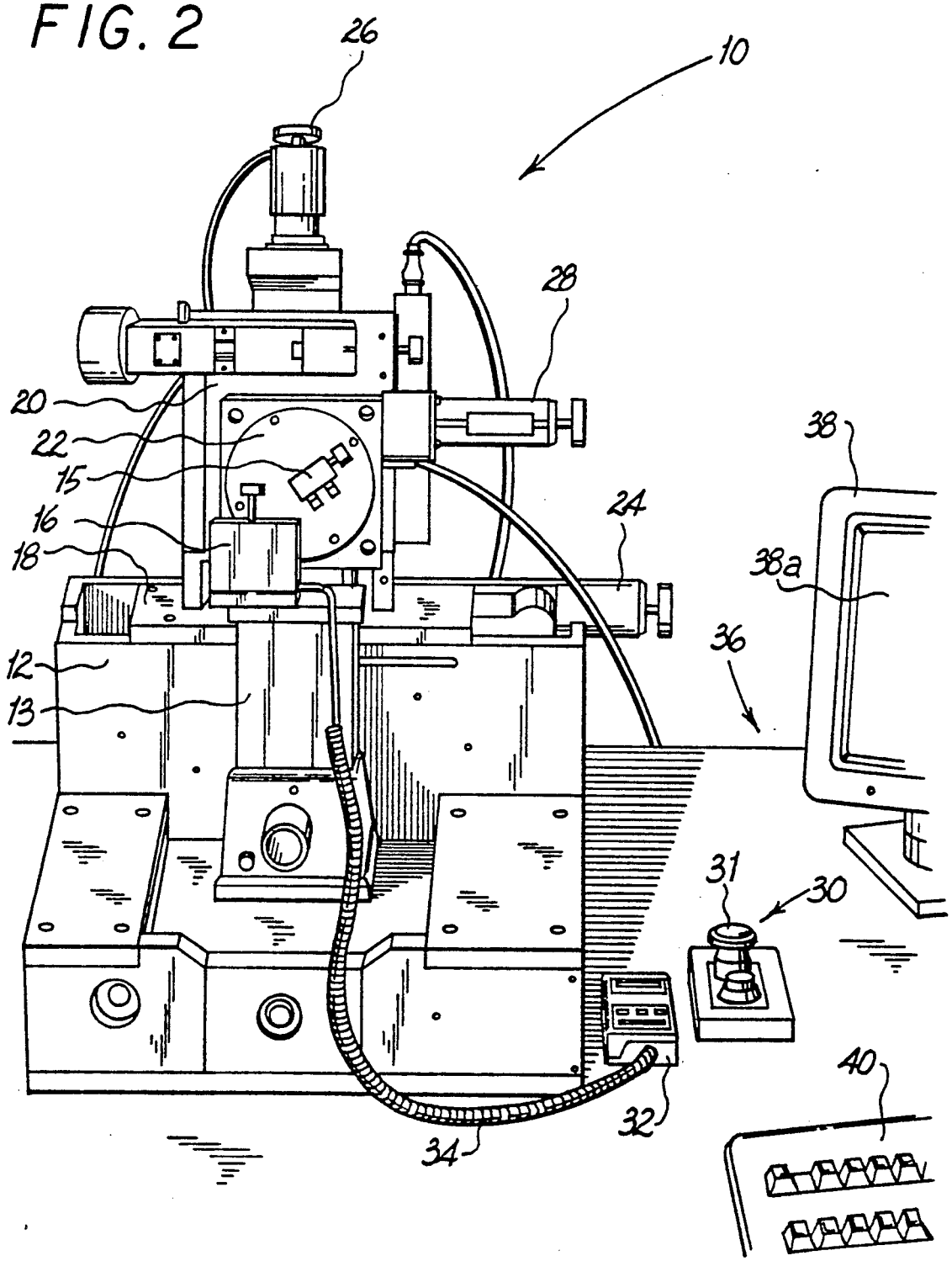
FIG. 2 is an overall front elevation view thereof.

Referring now to the drawings wherein like numerals represents identical parts throughout the several views, and more particularly to FIGS. 1 and 2, the bending moment tester 10 generally includes a support base 12, a minimum friction plate 14 slidably mounted on upstanding post 13 which is in turn attached to base 12, and a load cell 16 mounted on plate 14 which is slidable relative to post 13 with minimal frictional resistance.

Bending moment tester 10 further includes a horizontal plate 18 which is slidably mounted on base 12 for forward and afterward lateral movement. Horizontal plate 18 is also capable of right and left lateral movement. Vertical plate 20 is slidably mounted on horizontal slide plate 18 and circular table 22 is rotatably affixed to vertical slide plate 20 as shown. Although not illustrated in detail, horizontal plate 18 and vertical plate 20 are appropriately mounted by suitable bearings or other known devices to permit linear movement thereof with minimum frictional resistance when driven by the stepper motors as will be described. As will be described hereinbelow, such relatively synchronous movement permits the needle 17 to deform freely by the known forces and/or bending moments applied so as to facilitate measurement of such forces and/or bending moments with extreme precision. This is particularly facilitated when the maximum frictional resistance of plate 14 is less than any resistance to movement of the needle tip relative to the upper surface 16a of the load cell 16 and thereby permits needle 17 to bend freely under the applied load. Thus the needle tip 17a remains in the same location on upper contact surface 16a of load cell 16.

As seen in FIG. 1, clamp 15 is affixed to horizontal support arm 19 which in turn extends outwardly from rotary table 22 as shown for releasably gripping needle 17. Servo stepper motors 24, 26 and 28 are provided for driving horizontal slide plate 18, vertical slide plate 20 and rotary table 22 respectively. A manually operable controller panel 30 is arrangeed to control motors 24, 26 and 28 via control knob 31, for example, and to synchronize the motions of plates 18 and 20 and table 22 via push button 33, for example. This synchronized motion permits the needle to be deformed by the applied load while eliminating such unknown load factors which would otherwise be present if the plates positions were fixed.

As can be seen further from FIG. 2, load sensor 32 is connected to load cell 16 via cable 34 and is adapted to measure the forces applied to load cell 16 by needle 17 and to transmit the force data to data processing center 36 which includes monitor 38 and keyboard 40, for data storage and analysis. Data processing center 36 includes known hardware and appropriate software to plot the forces applied to load cell 16 and terminal 38 is adapted to display the plot of applied force vs. needle movement and to display this plot as a graph on screen 38a. Data processing center 36 is also adapted to generate and transmit appropriate instructions to controller 30 for any combination of synchronized movements between plates 18 and 20 and table 22.

Figure 3:
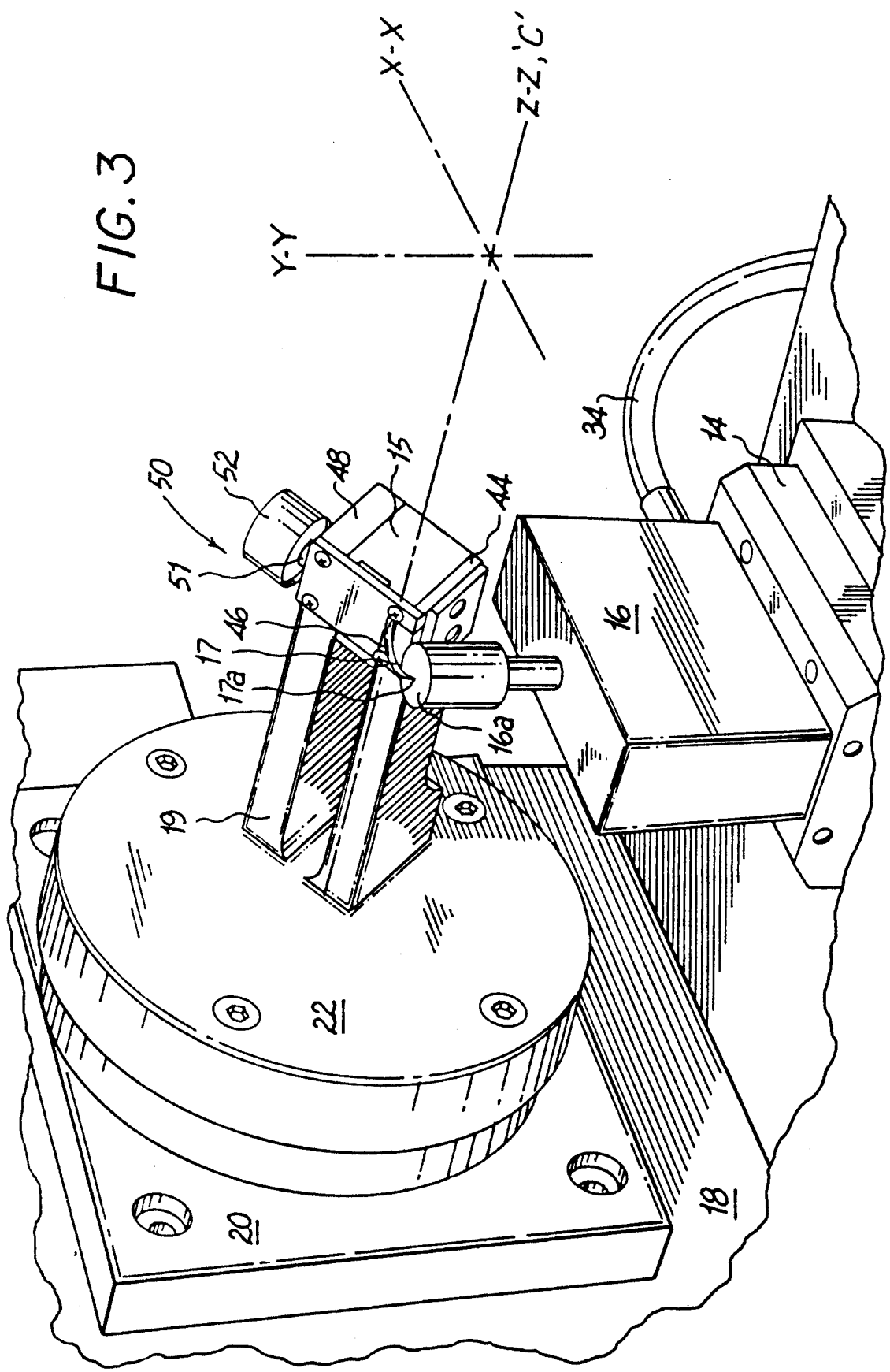
FIG. 3 is an enlarged perspective view of the needle changing zone of the apparatus of FIG. 1 showing an initial start position.
Figure 5:
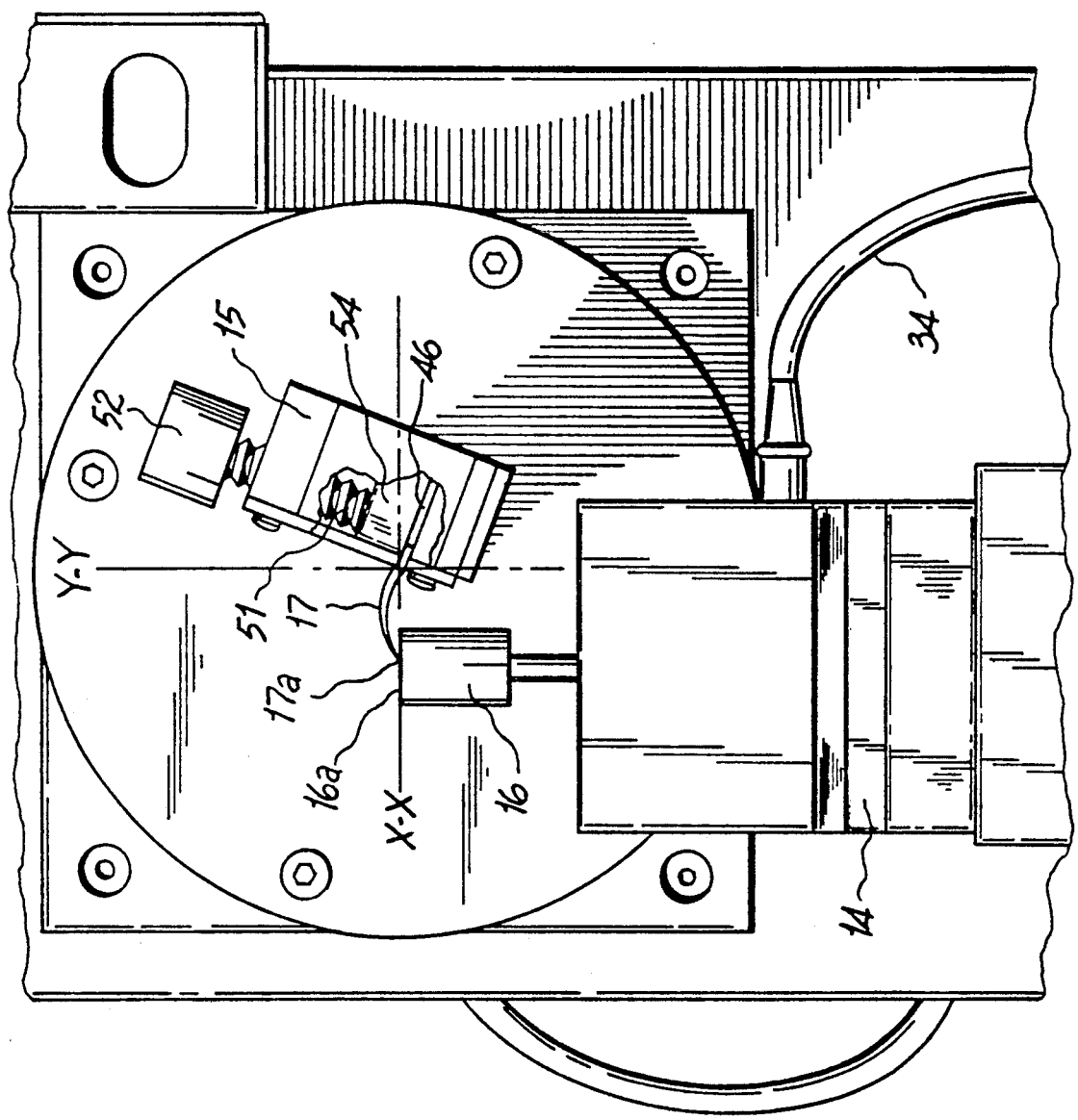
FIG. 5 is a front elevational view similar to FIG. 4, partially cut away to illustrate the needle gripping means in the gripping zone.
Figure 6:
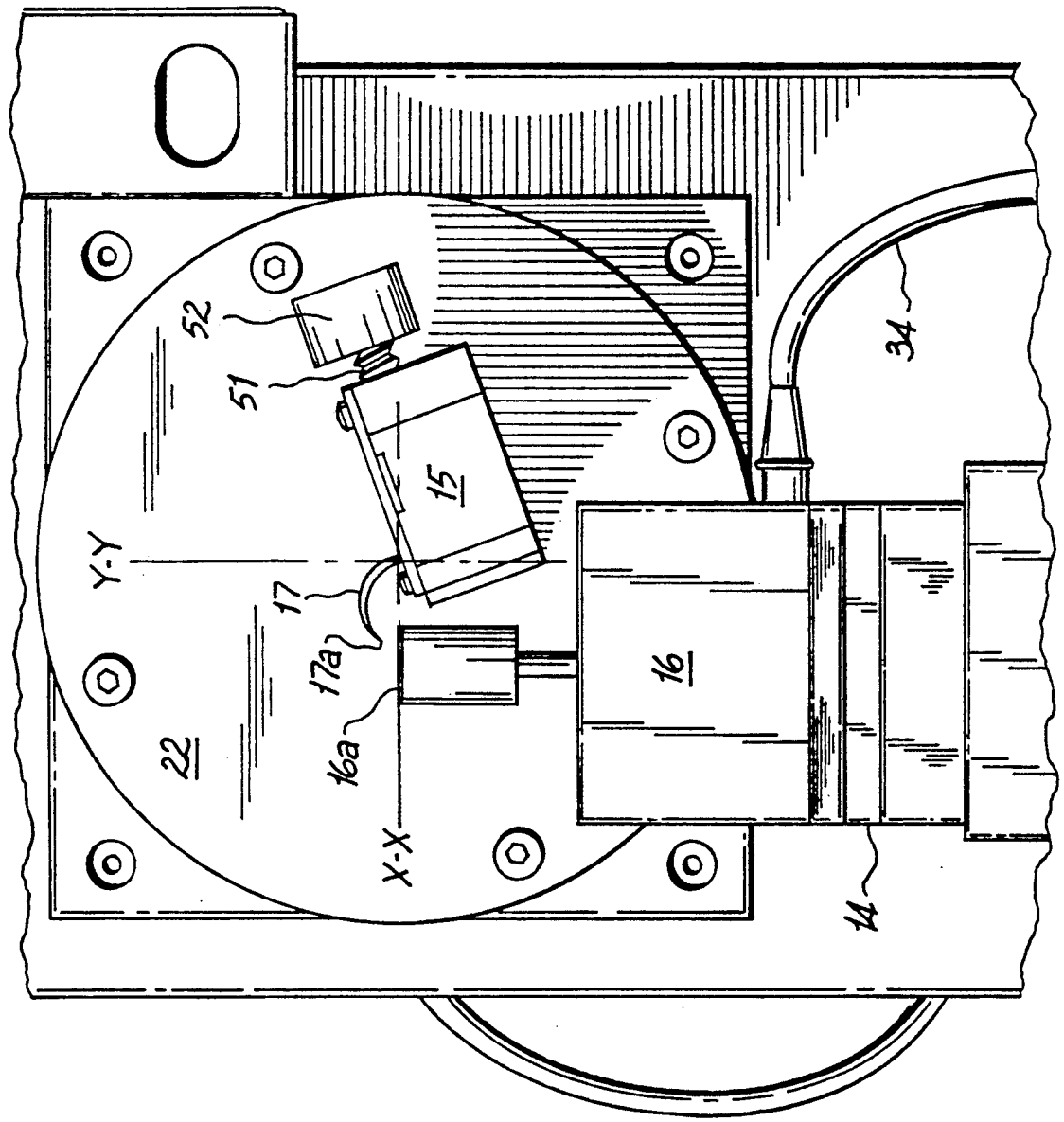
FIG. 6 is an enlarged front elevation view of the present invention showing the gripping means rotated back to its initial position.

With reference now to FIG. 3, in conjunction with FIGS. 1, 2 and 5 it can be seen that clamp 15 is rigidly affixed to rotary table 22 via support arm 19 such that the inner gripped surface of needle 17 is positioned at the center of rotation of rotary table 22. Clamp 15 is of known type and includes a front plate 44 having a needle groove 46 for receipt of curved surgical needle 17 as shown. Rear end portion 48 includes threaded aperture (not shown) to threadedly receive threaded shaft 51 having a manually operable knob 52 connected thereto. Threaded shaft 51 also includes a binder 54 for holding needle 17 in groove 46 as shown in FIG. 5.

Figure 4:
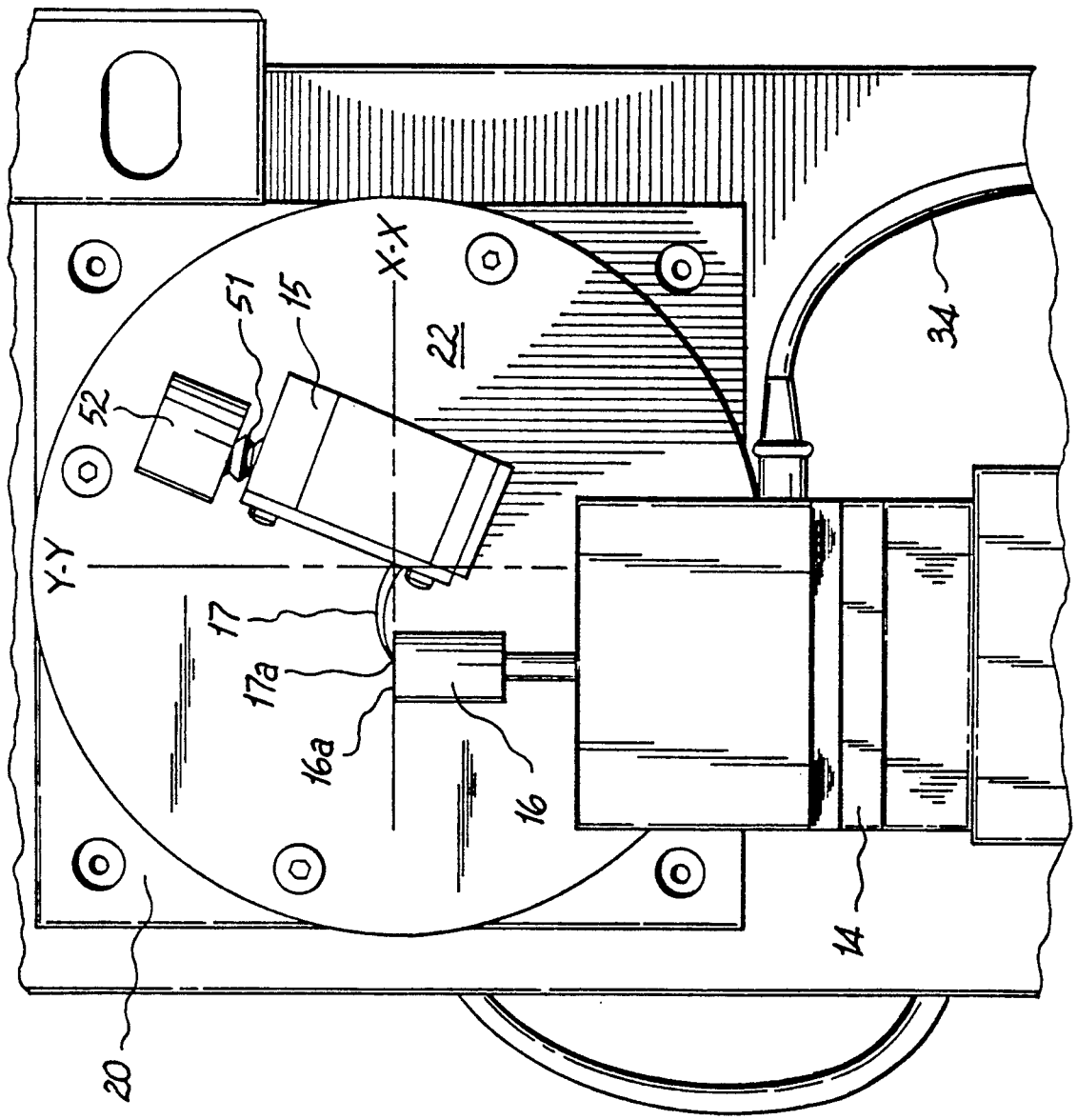
FIG. 4 is an enlarged front elevation view of the needle changing zone showing the needle gripping means rotated approximately through one half cycle.

As can be seen clearly in FIGS. 3 and 4 and as noted hereinabove, the center of rotation of the inner gripped surface of needle 17 is located at the center of rotation of rotary table 22 to simulate as precisely as possible the actual forces exerted on the needle by a surgeon during suturing. In particular, the multi-directional forces and bending moments to which the curved needle is normally subjected during surgical use are being simulated to an enhanced degree.

The bending moment tester 10 of the present invention is capable of moving needle 17 along 3 linear axes of motion, (i.e., "X—X", left and right, "Z—Z" fore and aft) in the horizontal directions by movement of the horizontal slide plate 18 respectively in those directions. The vertical direction is defined by movement along axis "Y—Y" (up and down) as best shown in FIG. 4, and needle movement along the "Y—Y" direction is obtained by movement of vertical slide plate 20 in those directions. Rotational movement of needle 17 is obtained by respective clockwise and counterclockwise rotation of rotary table 22 about axis "Z—Z". More significantly, bending moment tester 10 is further capable of synchronized compound motion about any two or more of the aforementioned axes. Thus bending moment tester 10 may be used to test the bending moments applied to a surgical needle when subjected to linear or rotary forces, or any combination thereof.

In operation surgical needle 17 is inserted into groove 46 and firmly held in place by binder 54 as shown in FIG. 5. Clamp 15 is rotated with table 22 to form an angle of approximately between 10° and 30° with regard to a horizontal reference plane. As shown in FIG. 3, the position of load cell 16 is adjusted by movement of minimum friction slider plate 14 and linear tables 18 and 20 until the tip 17a of needle 17 rests on top of surface 16a of load cell 16. The initial arm length from the center of rotation "C" to tip 17a of needle 17 as measured by known means on load cell surface 60 is entered into data processing center 36 via keyboard 40. Thereafter a series of movements of the stepper motor 24, 26, 28 may be programmed into data processing center 36 to initiate a rotational or linear loading test, or any combination thereof, of needle 17. For example, in a rotational test of needle 17, tip 17a is moved against load cell 16 first up to 90° counterclockwise to a half cycle position as shown in FIG. 4, and thereafter rotated 90° clockwise to its initial position as shown in FIG. 5. The resulting forces on the load cell are transmitted to data processing center 36 during the rotational movement by load sensor 32 and the results are displayed on video terminal 38 as a plot of load vs. angular rotation.

In a preferred application of the apparatus the load cell upper surface and the center of rotation "C" are predetermined to lie on the same horizontal line and tip 17a of needle 17 is rotated into load cell 16 by rotation of rotary table 22. As needle 17 is rotated it undergoes a change in configuration such that tip 17a tends to move away from clamp 15 as opposed by stepper motor of plate 14 along axis "X—X" and toward the left side of FIG. 2. In addition, horizontal slide table 18 is programmed to moved in synchronized fashion with the rotation of rotary table 22 to prevent needle 17 from slipping on load cell top surface 16a during rotation. In the preferred use of apparatus 10, needle 17 is rotated counterclockwise approximately 30° and thereafter clockwise 30° to generate a representative load curve. Rotational speed is preferably between about 2° and 5° per second while synchronized horizontal movement distance is typically about one third of the arm length of the rotational arm as previously measured and entered into the data processing center.

A linear test may be performed of needle 17 utilizing the same initial set up described hereinabove. In use vertical table 20 is programmed for movement through a cycle in one direction and thereafter returned to its initial position thereby generating a force curve which can then be displayed on terminal 38 or stored in data processing center 36 for later analysis. During such a test, the movement of horizontal table 18 is synchronized with the loading movement of vertical table 20 to minimize slippage of tip 17a on surface 16a. In a preferred use of the linear test, needle 17 is moved through a vertical cycle a distance of approximately 100 mils (i.e., millimeters) with a vertical speed of approximately 10 mils/sec.

It can be appreciated that with minor modifications to clamp 15, bending moment apparatus 10 may also be used for testing micro-surgery needles, and with still other modifications, bending moment apparatus 10 is also readily capable of being used for penetration testing.

What is claimed is:

1. An apparatus for determining the bending characteristics of a curved surgical needle having a butt end portion and a tip portion which comprises:
    a) support means;
    b) means associated with said support means for releasably gripping the butt end portion of the needle;
    c) means for moving said gripping means and the needle along a predetermined path;
    d) means positioned within said predetermined path for engagement by the tip of the needle;
    e) means for sensing the forces applied to said engagement means by the needle tip; and
    f) means to maintain the needle tip at a predetermined location on said engagement means while moving said gripping means and the needle.

2. The apparatus according to claim 1 wherein said means for releasably gripping the needle comprises clamping means.

3. The apparatus according to claim 1 wherein said means for moving said gripping means comprises a first table arranged and adapted for linear movement.

4. The apparatus according to claim 3 wherein said means for moving said gripped needle further comprises a second table arranged and adapted for rotational movement and mounted with respect to said linearly movable table for rotatably supporting said needle gripping means.

5. The apparatus according to claim 4 further comprising respective stepper motors to move said first and second tables.

6. The apparatus according to claim 5 wherein said first table is mounted on bearing support means adapted to facilitate table movement with minimal frictional resistance.

7. The apparatus according to claim 5 wherein said stepper motors are respectively controlled by controller means adapted to control said motor according to predetermined instructions.

8. The apparatus according to claim 4 wherein the center of rotation of said needle coincides with the center of rotation of said second table.

9. The apparatus according to claim 4 wherein said needle locating maintaining means includes means to synchronize movement of said first and second tables.

10. The apparatus according to claim 1 wherein said sensing means is in the form of load cell means positioned, adapted and arranged to engage the needle tip.

11. The apparatus as recited in claim 10 wherein the upper surface of said load cell means is adapted and positioned to engage the needle.

12. The apparatus as recited in claim 1 wherein minimal friction support means is provided to support said needle locating maintaining means.

13. An apparatus for determining the bending characteristics of a curved surgical needle having a butt end and a tip comprising:
   a) means for releasably gripping the butt end of the needle;
   b) means for moving the gripped needle along a path having a plurality of axes;
   c) means positioned within said path of the gripped needle for interaction with the tip of the needle;
   d) means for sensing the forces applied to said interaction means by the needle tip; and
   e) means for synchronizing the needle movement to permit deformation of the needle without relative movement between the needle tip and said sensing means.

14. The apparatus according to claim 13 wherein said means for moving the gripped needle comprises a plurality of movable plates for movable support of said gripping means, said plates adapted to move in synchronized fashion.

15. An apparatus for measuring the bending moment of a curved surgical needle which comprises:
   a) a base support;
   b) a low friction plate slidably mounted on said base support;
   c) a load cell mounted on said low friction plate;
   d) a horizontal slide table slidably mounted on said base support;
   e) a vertical slide table slidably mounted on said horizontal table;
   f) a rotary table rotatably mounted on said vertical table;
   g) a clamp affixed to said rotary table for releasably gripping the needle;
   h) a plurality of stepper motors adapted and arranged for driving said tables to move the elongated needle mounted in said clamp into engagement with said load cell and to provide synchronous movement of said horizontal slide table and said vertical slide table and the frictional resistance to movement of said low friction plate is less than the resistance to movement of the needle tip relative to said load cell to thereby permit uninhibited defomation of the needle.

16. An apparatus for testing the bending resistance of a curved surgical needle having a butt end portion and a pointed tip which comprises:
   a) a base support;
   b) a low friction plate slidably mounted on said base support;
   c) a load cell mounted on said low friction plate;
   d) a horizontal slide table slidably mounted on said base support;
   e) a vertical slide table slidably mounted on said horizontal table;
   f) a rotary table rotatably mounted on said vertical table;
   g) a clamp affixed to said rotary table for releasably gripping the butt end portion of the needle;
   h) a plurality of stepper motors for driving said tables to move said elongated needle mounted in said clamp into engagement with said load cell; and
   i) means to synchronize the movements of said tables to permit the needle to deform without relative movement between the needle tip and said load cell.

17. The apparatus according to claim 16 wherein at least one of said stepper motors is adapted to cause said rotary table to rotate so as to cause the needle tip to engage said load cell.

18. A method of determining the bending characteristics of a curved surgical needle having a butt end portion and a pointed tip comprising:
   a) releasably gripping the butt end portion of the needle;
   b) moving the needle along a predetermined path;
   c) obstructing the movement of the tip of the needle;
   d) maintaining the position of the tip of the needle on the obstruction; and
   e) generating a signal proportional to the forces which the needle tip exerts during said obstructing step.

19. The method according to claim 18 wherein the needle is moved along a plurality of axes in synchronized manner to permit the needle to deform while avoiding relative movement between the needle tip and said obstructing means.

20. The method according to claim 18 wherein said obstructing means is load cell means.

21. The method according to claim 18 wherein said signal generating means is a sensor adapted to generate a signal dependent on the forces applied to said load cell means.

* * * * *